(12) United States Patent
Taylor

(10) Patent No.: US 6,410,053 B1
(45) Date of Patent: *Jun. 25, 2002

(54) REVERSIBLE CROSS-LINKED GEL

(75) Inventor: Margaret Joan Taylor, Hoton Nr Loughborough (GB)

(73) Assignee: De Montfort University, England (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/124,445

(22) Filed: Jul. 29, 1998

Related U.S. Application Data (63) Continuation of application No. 08/569,119, filed as application No. PCT/GB94/01384 on Jun. 27, 1994.

(30) Foreign Application Priority Data

Jun. 30, 1993 (GB) ............................................. 9313484

(51) Int. Cl.[7] .......................... A61K 9/10; A61K 47/42; A61K 47/36

(52) U.S. Cl. ........................ 424/488; 424/484; 514/944

(58) Field of Search ...................... 424/28.01, 484–486, 424/488, 422, 423; 514/944, 773

(56) References Cited

FOREIGN PATENT DOCUMENTS

| WO | 8100354 | 2/1981 |
|----|---------|--------|
| WO | 9217167 | 10/1992 |
| WO | 9313803 | 7/1993 |

*Primary Examiner*—Edward J. Webman
(74) *Attorney, Agent, or Firm*—Renner, Otto, Boisselle & Sklar (57) ABSTRACT

There is disclosed a method for producing a system for delivering a drug for the treatment of a condition, comprising immobilizing a drug or other agent in a bio-compatible matrix containing at least one receptor for a physiological substance which will be in the environment of the matrix when administered, said receptor being anchored within the matrix but remaining biologically active being activated in response to the levels of said physiological substance to effect a conformational change in the matrix allowing mobilization and release of the drug only into the environment.

20 Claims, 9 Drawing Sheets

REVERSIBLE CROSS-LINKED GEL

This application is a con't of Ser. No. 08/569,119 filed Mar. 27, 1996 which is a 371 of PCT/GB94/01384 filed Jun. 27, 1994.

This invention concerns a method for producing a drug system for delivering a drug or other agent for the treatment of a condition in a controlled release manner.

Most known 'controlled-release' drug systems are constant slow-release mechanisms (U.S. Pat. No. 4,145,410). These systems do not react to any inherent substances in the body to release the drug appropriately in response to that substance, ie. there is no feedback mechanism. Feedback mechanisms have been suggested to be of interest in vivo to maintain general homeostasis.

U.S. Pat. No. 4,348,387 discloses a feedback controlled insulin delivery system wherein glucose-insulin conjugates are displaced from glucose binding sites on a binding molecule by free glucose. The conjugated insulin retains its biological activity once released. However, it is not known whether other agents or drugs can be so conjugated or whether such a conjugated form of any drug or other agent would be effective.

The present invention provides a delivery system for the controlled release of an unconjugated drug or other agent for possible use in vivo.

According to the present invention there is provided a method for producing a system for delivering a drug for the treatment of a condition, comprising immobilising a drug or other agent in a bio-compatible matrix containing at least one receptor for a physiological substance which will be in the environment of the matrix when administered, said receptor being anchored within the matrix but remaining biologically active being activated in response to the levels of said physiological substance to effect a conformational change in the matrix allowing mobilisation and release of the drug only into the environment.

The agent may comprise a naturally occurring biological agent, for example, a hormone, which may, of course, be insulin, as in U.S. Pat. No. 4,348,387, but now in unconjugated form. Because there is now no need for conjugation, other hormones or drugs which it may not be possible to conjugate or which will not work in the system of U.S. Pat. No. 4,348,387 even if they can be conjugated, or which may be physiologically ineffective or less effective or even harmful when conjugated, may be used according to the invention.

The receptor may be a binding macromolecule, for example, a lectin, which may be concanavalin-A, a lectin produced from the jack bean. Because the binding macromolecule is anchored within the matrix, it is not necessary to enclose the system within a semi-permeable membrane, tube or other device, as is the case in the system of U.S. Pat. No. 4,348,387. Such a method of restraining the drug system may alter the kinetics of the drug releasing mechanism and result in reduced sensitivity. Additionally, should the retaining device disintegrate, toxic lectin molecules would be released into the general circulation. The present invention provides a system which overcomes these disadvantages and allows lectins to be used more safely.

The receptor may reversibly bind the physiological substance, which may be a carbohydrate, preferably glucose, fructose or mannose or a carbohydate polymer containing glucose moieties, such as branched starches, dextrans, mannans and levans or synthetic carbohydrates, for example, ficoll-400, a synthetic polysucrose.

Insulin, or any other agent or drug, may be immobilised in the matrix when terminal glucose molecules on dextran bind to concanavalin-A to form a gel.

Concanavalin-A molecules are anchored within the matrix by covalent bonding to the polymeric chains of dextran without-forming insoluble aggregates. Such a system allows maintenance of the structure and function of the matrix. The concanavalin-A may be covalently bonded to the dextran in any conventional manner, for example;

via the sodium iodate oxidation to Schiff bases of vicinial OH groups on dextran, followed by reduction and purification by precipitation;

via azide bonding to linear polyacrylamide hydrazide;

via glutaraldehyde bonding to linear polyacrylamide.

The conformational change in the matrfix may be brought about by the displacement of terminal dextran-glucose molecules from the receptor by free glucose in the physiological environment which may of course be blood or other tissue fluid or fluid in the lumen of the digestive tract.

The conformational change may be an ungelling of the matrix allowing mobilisation and release of the insulin or other agent or drug.

The drug system may be specific to monosaccharides including αD-mannose, α-D-glucose and α- and β-fructose and disaccharides including maltose and di-glucose with an α-linkage.

The drug system may-not be affected by changes in pH from 4.0 to 8.0 nor by changes in the $Mn^{++}$ or $Ca^{++}$ ion concentration of the surrounding environment.

The drug system may be presented to a patient in vivo in a number of ways, for example, orally using oral hypoglycaemic drugs (insulin may not be used orally as it would not be absorbed in an active form) or by a subcutaneous implant, for example.

The invention will be further apparent from the following description with reference to the several figures of the accompanying drawings, which show, by way of example only, one form of the system embodying same.

Figure 1:
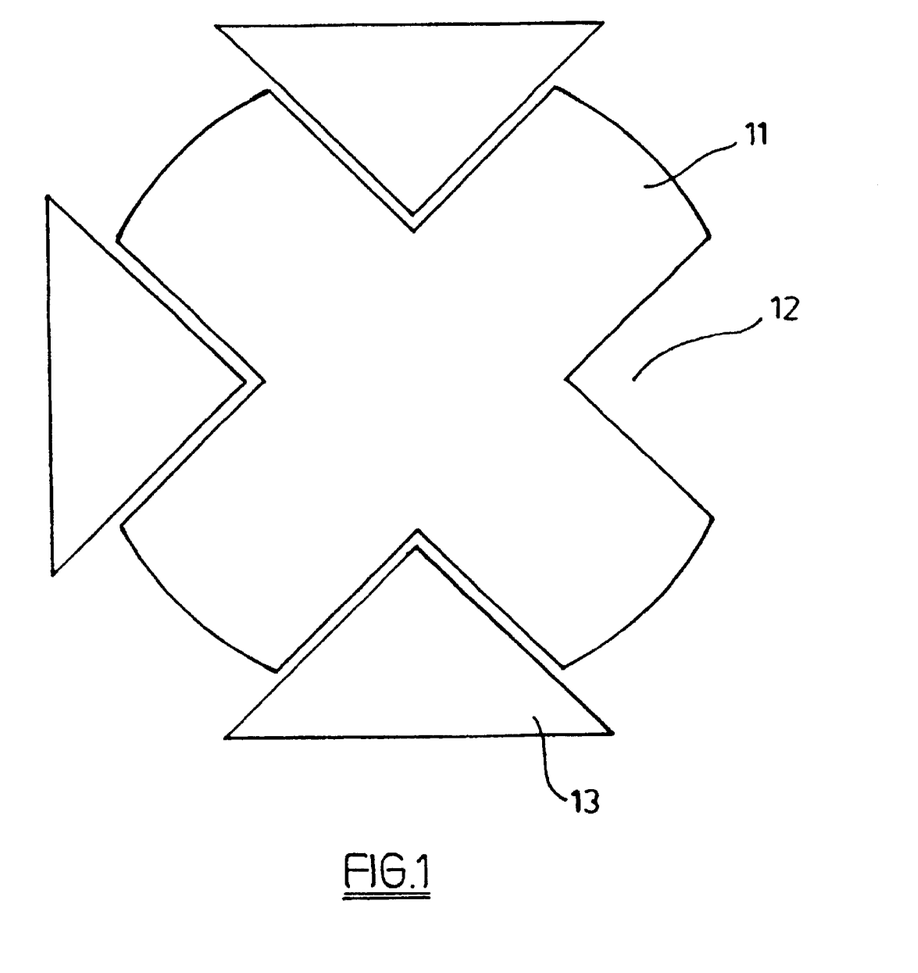
FIG. 1 shows a diagrammatical representation of a concanavalin-A molecule binding glucose.

Referring now to the drawings, it will be seen that the drug delivery system is based on a concanavalin-A molecule 11. Each concanavalin-A molecule 11 has four binding sites 12 specific for sugars, with a high affinity for glucose 13 (FIG. 1). The binding of glucose 13 to the binding site 12 is, however, reversible.

Figure 2:
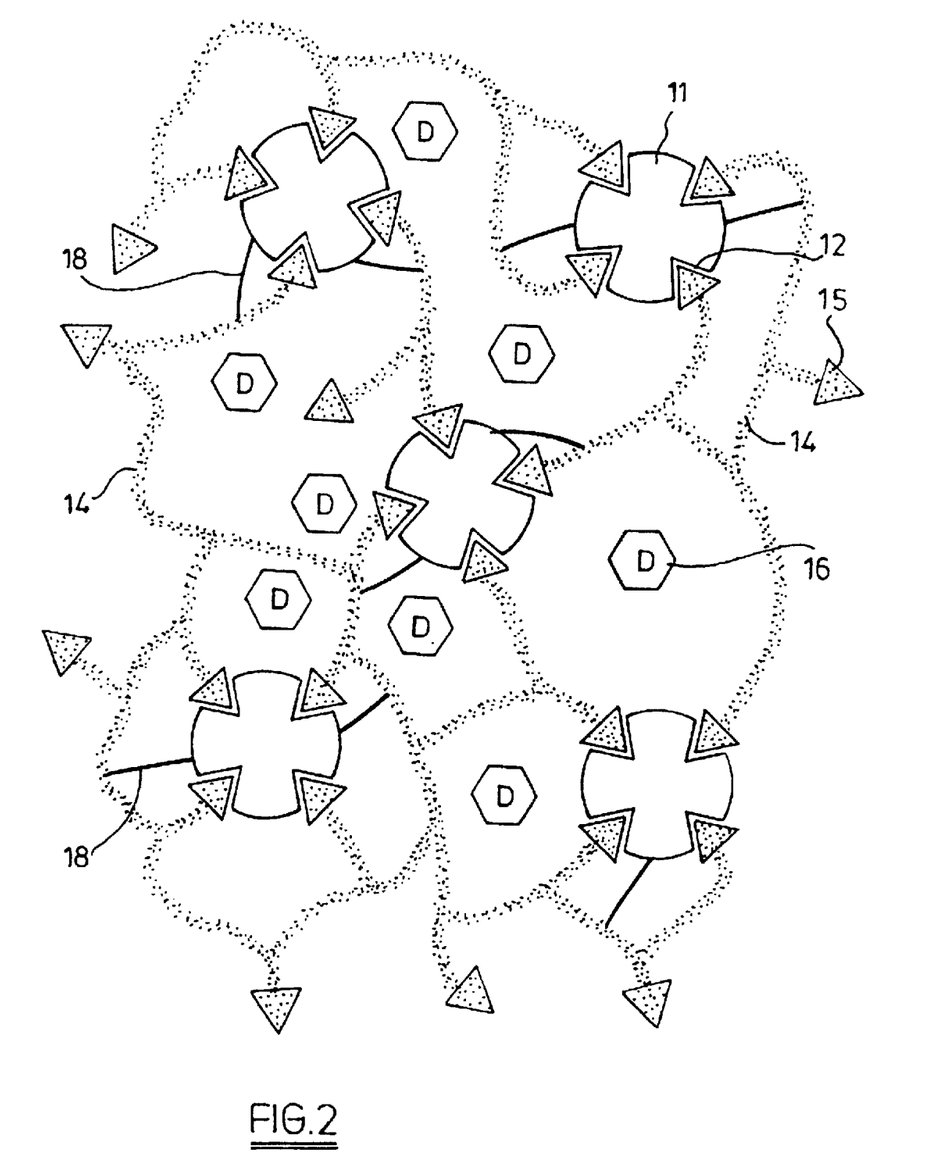
FIG. 2 shows a diagrammatical representation of the delivery system, in an inactive form.

The inactive form of the drug system comprises (FIG. 2) glucose present as terminal glucose moieties 15 of the carbohydrate dextran. Dextran is a branched chain polysaccharide with many terminal glucose moieties which can bind to the binding sites 12 of concanavalin-A molecules 11 and in so doing cross-link the concanavalin-A molecules together to form a viscous gel matrix. Concanavalin-A molecules are covalently bonded 18 to dextran polymeric chains 14, leaving the binding sites 12 of concanavalin-A molecules 11 free to react with glucose molecules 15. Insulin 16 is premixed with dextran gel, so that when concanavalin-A is added to the mixture, a gel is formed between the dextran and the concanavalin-A with the insulin immobilised inside the gel matrix much restricted in its rate of escape (FIG. 2).

The binding of terminal glucose moieties of dextran to concanavalin-A is reversed (FIG. 3) when there is an increase in the concentration of free glucose 17 in the physiological environment. The free glucose displaces the terminal dextran-glucose 15 from the binding sites of the concanavalin-A molecules. The matrix undergoes a conformational change allowing mobilisation and release of the insulin into the environment. Concanavalin-A molecules 11 remain anchored to the dextran via covalent bonds 18.

Figure 3:
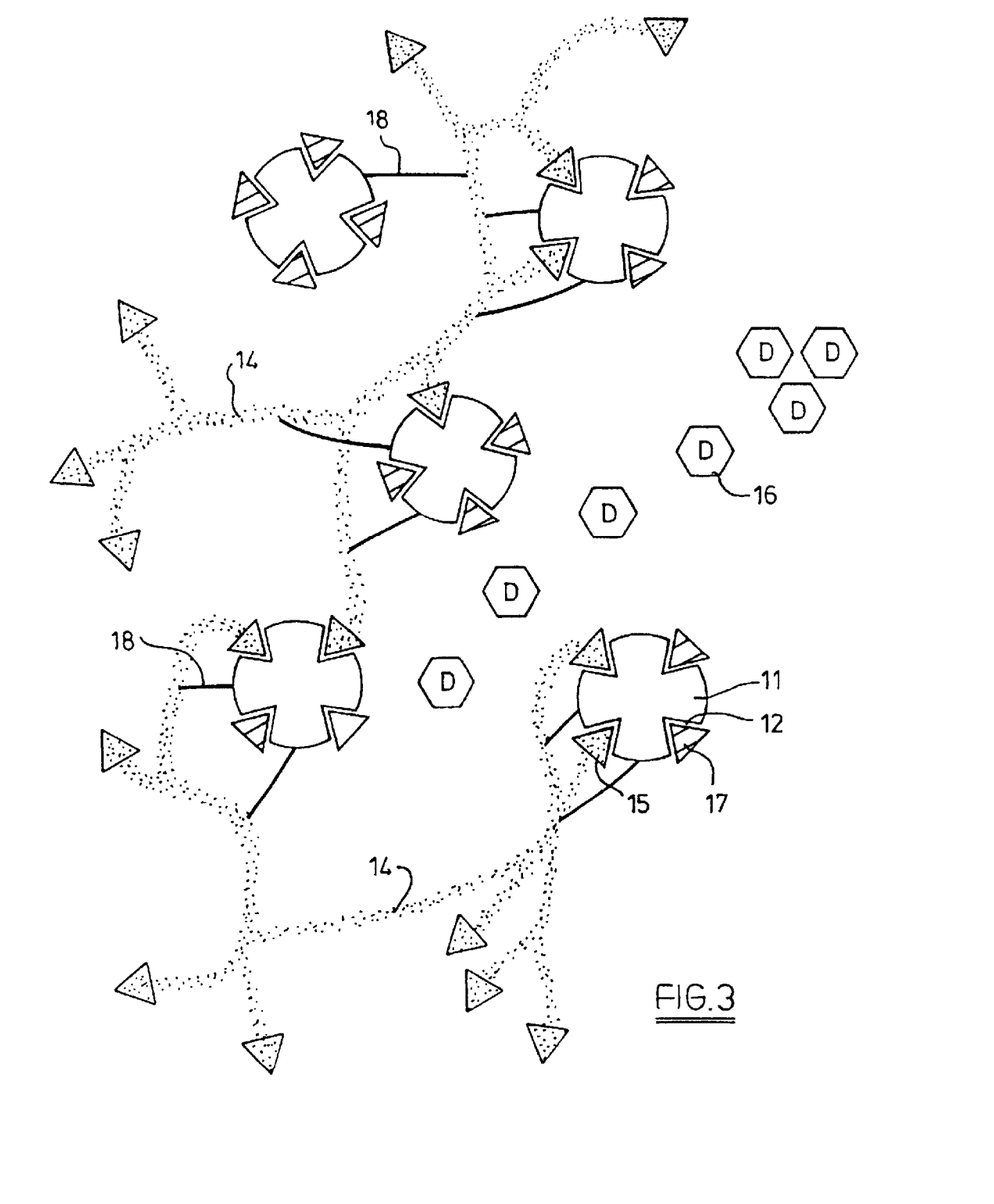
FIG. 3 shows a diagrammatical representation of the delivery system, in an active form.

Once the level of free glucose falls, in response to the action of the released insulin, the displaced terminal dextran-glucose mnolecules will re-bind to the concanavalin-A molecules and the matrix will re-gel, thus again restricting insulin remaining in the matrix.

The mechanism of this drug system is thus repeatable and releases insulin in response to a number of free glucose insults, in a manner which mimics the in vivo feedback mechanism of the pancreatic cells.

Experimnents were carried out in vitro to test the sensitivity of the drug system under various conditions by measuring the release of a model marker substance tartrazine therefrom.

Two types of gel systems were prepared as follows:
1. Simple System 400 mg polysucrose 400 and 75 mg tartrazine were mixed and made up to 1 g with water and allowed to hydrate. This solution was added to an aqueous solution containing 200-mg concanavalin-A in 1 g, mixed well until gelled and stored between 4–10° C. for 24 hours before use.

2. Covalently Bonded System 100 mg dextran 500,000 was made up to 0.5 g with water, allowed to hydrate and mixed well. 10 mg sodium iodate in 0.5 mg water was added, mixed and left to stand for 20 minutes. 0.5 g of an aqueous solution containing 200 mg concanavalin-A was then added, mixed until gelled and allowed to stand for 5 minutes. 0.5 g of an aqueous solution containing 10 mg sodium borohydride was added in a fume cupboard and stirred until any foam had dispersed and any yellow colouration turned white. 96% ethanol was then added dropwise until precipitation occurred and the precipitate was filtered and washed with more ethanol. The precipitate was dried and rehydrated by making up to 2 g with distilled water. Precipitation was repeated a number of times. Finally, polysucrose 400 was added to a concentration of, for example, 15% and the precipitate rehydrated by making up to 2 g with water. The 2 g samples of gel also contained 75 mg tartrazine. The gel was mixed well and stored between 4–10° C. for 24 hours before use.

Diffusion Experiments

A diffusion cell was set up comprising two cellulose filters of pore size between 0.025 μm–0.45 μm (e.g. Whatman cellulose 0.1 μm pore size) spaced by a ring gasket ⅛" in thickness. The gel was placed in the gap between the membranes and was made bubble free and contained a loading dose of tartrazine. On one side of the cell was a reservoir containing a supersaturated solution of tartrazine (15%, above 15° C.) and on the other side was a bulk solution (usually purified water) into which could be added sugar or other test additives to simulate the environment of the clinical device. The bulk solution and diffusion cell were stirred and the bulk solution sampled and tested at 5 minute intervals or continuously via a flow through system.

Figure 4:
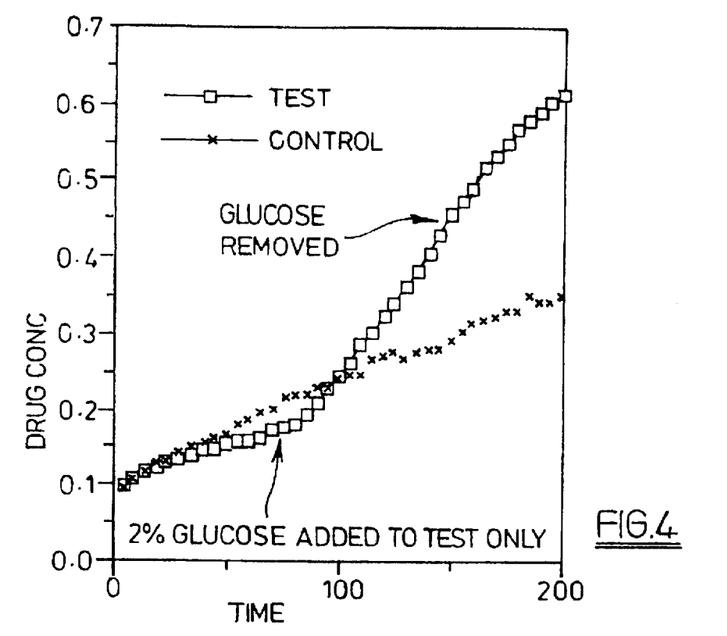
FIGS. 4 to 10 show in vitro experimental results of the drug system.
Figure 5:
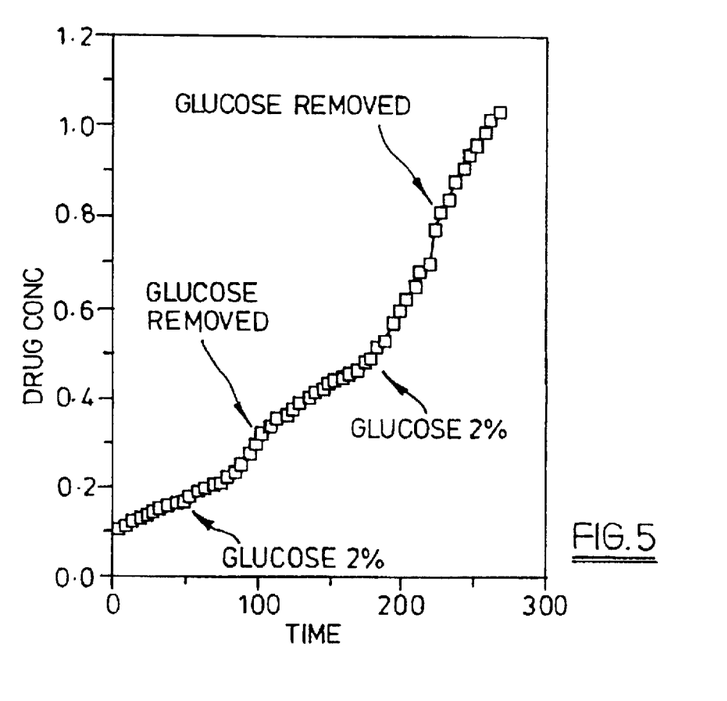

Results:—FIG. 4 shows an increased release of tartrazine into the bulk solution in the presence of 2% glucose compared to the control experiment (ie. no glucose). The increase in flux was approximately 2-fold. FIG. 5 shows the system working in response to fluctuations in the environmental glucose concentration in an attempt to mimick the situation in diabetes. After exposure to a 2% glucose solution, the bulk solution was replaced with a glucose free solution and the system monitored as before. Again there was an increased release of tartrazine from the system in the presence of glucose which was reversed in the absence of glucose.

Figure 6:
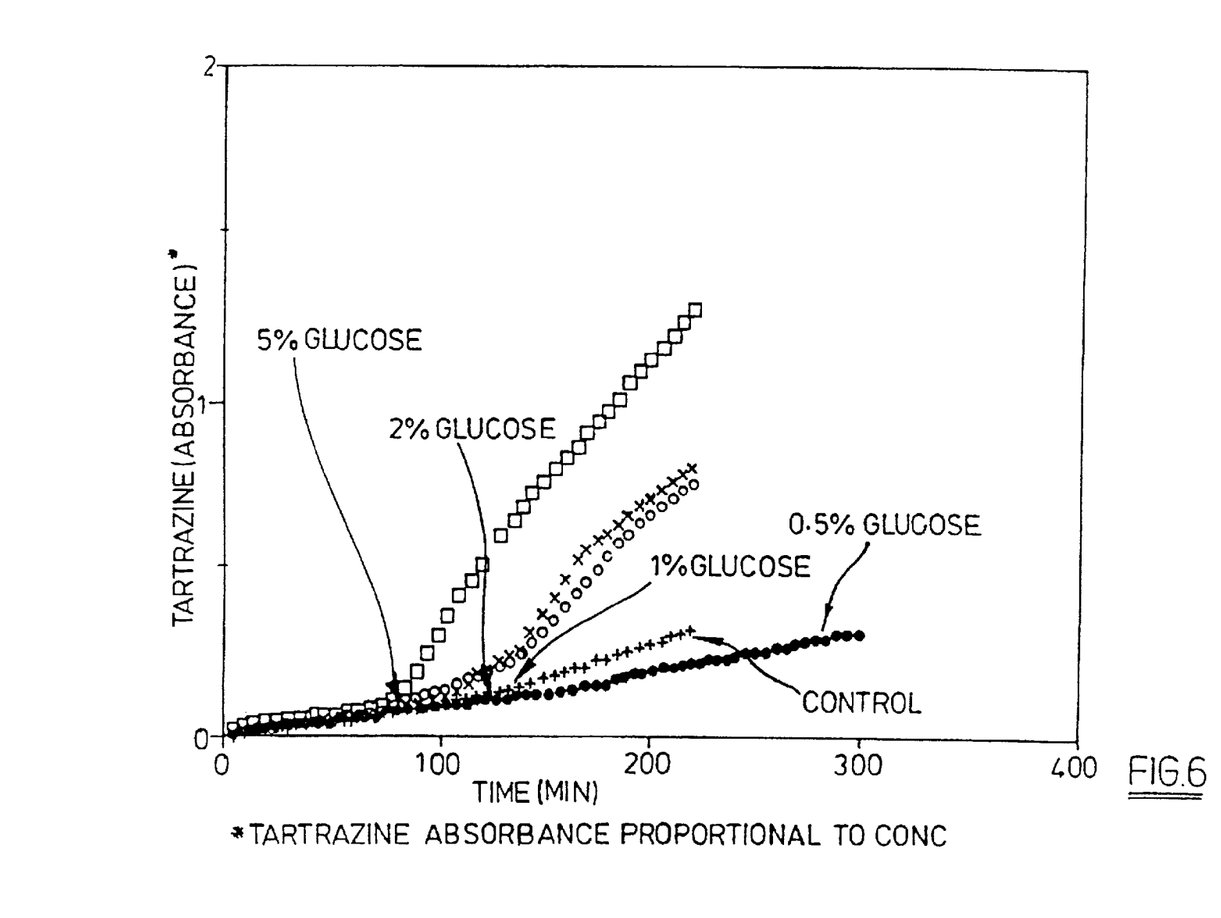

FIG. 6 shows the system responding to glucose concentrations between 1% and 5%. The magnitude of response does not appear to be related to the concentration used. The addition of 0.5% glucose appeared not to elicit a response.

Figure 7:
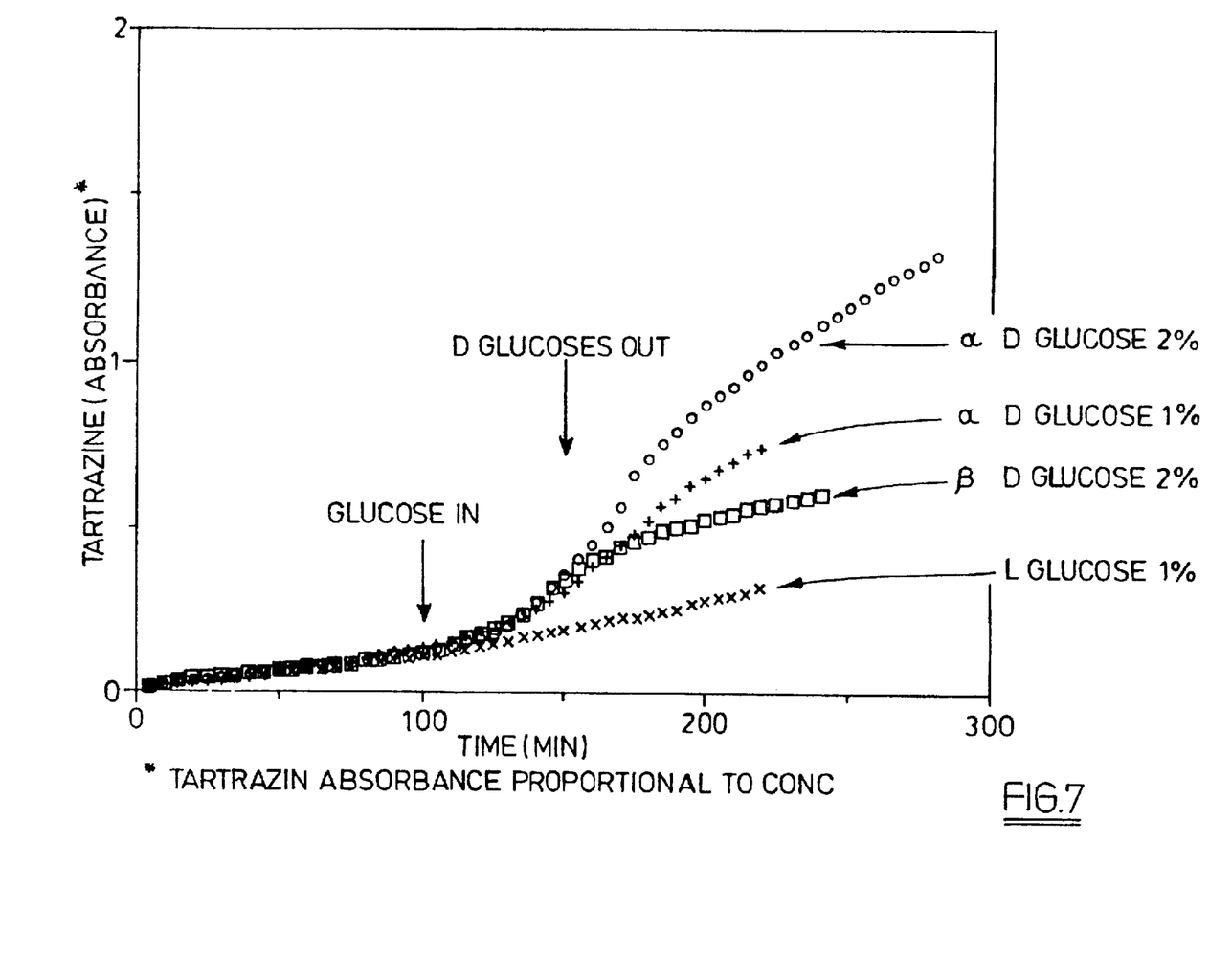

FIG. 7 shows the specificity of the system. The system is highly specific, the flux of tartrazine responding to monosaccharides α-D-mannose, α-D-glucose, and α- and β-fructose. Conversely, L-glucose produced no response, there being no complementarity with the lectin receptor. There was also no response with α-D-galactose. In the case of di-saccharides, there is no response to lactose or cellibiose but maltose and di-glucose with an α-linkage produced a response (not shown).

Figure 8:
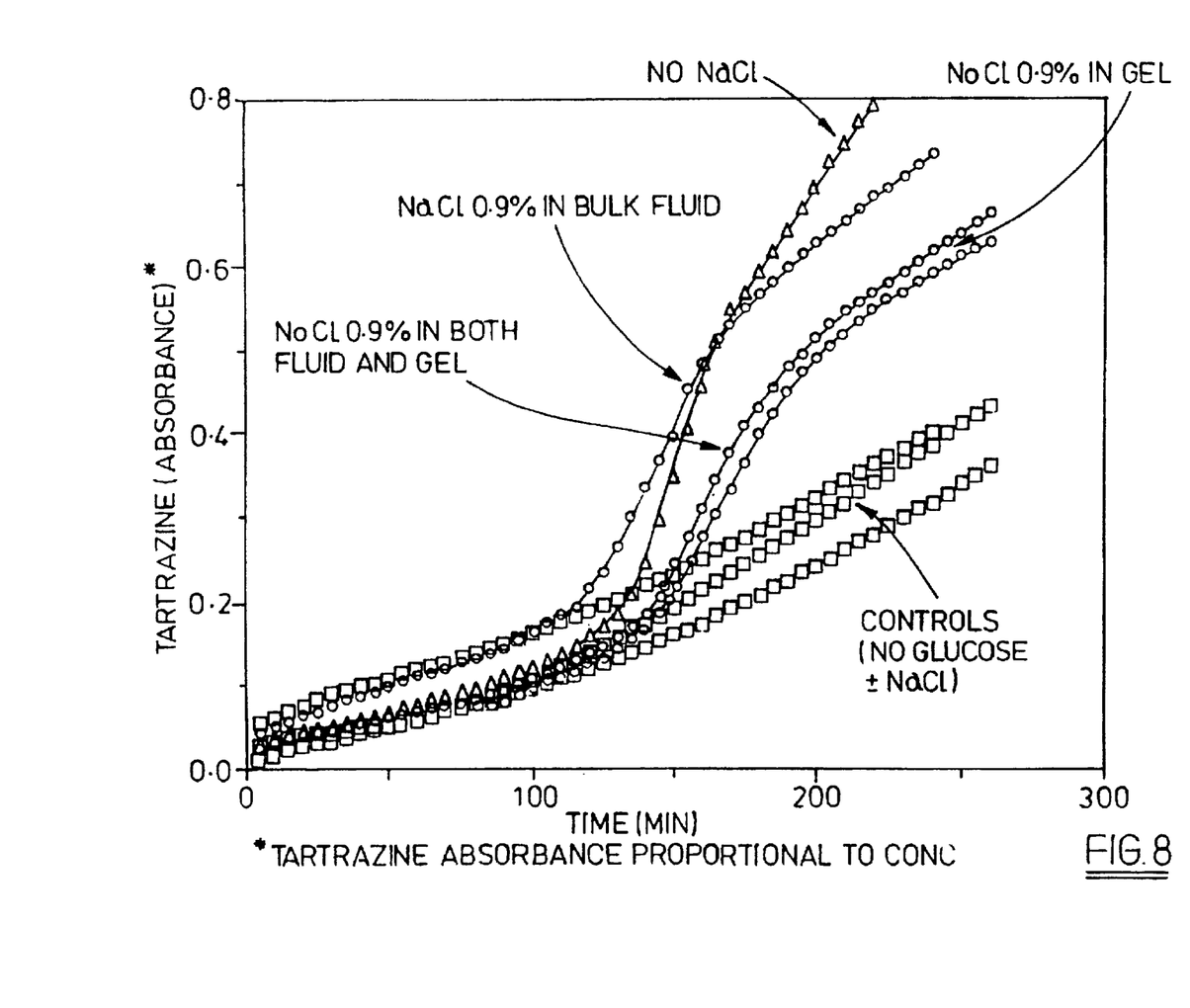

FIG. 8 shows the response of the system to salts. No respose to the sensitivity of the system was seen with 0.3% to 1% NaCl additions to the bulk solution in the presence or absence of glucose, thus ruling out the possibility that the gel was responding to an osmotic change.

Figure 9:
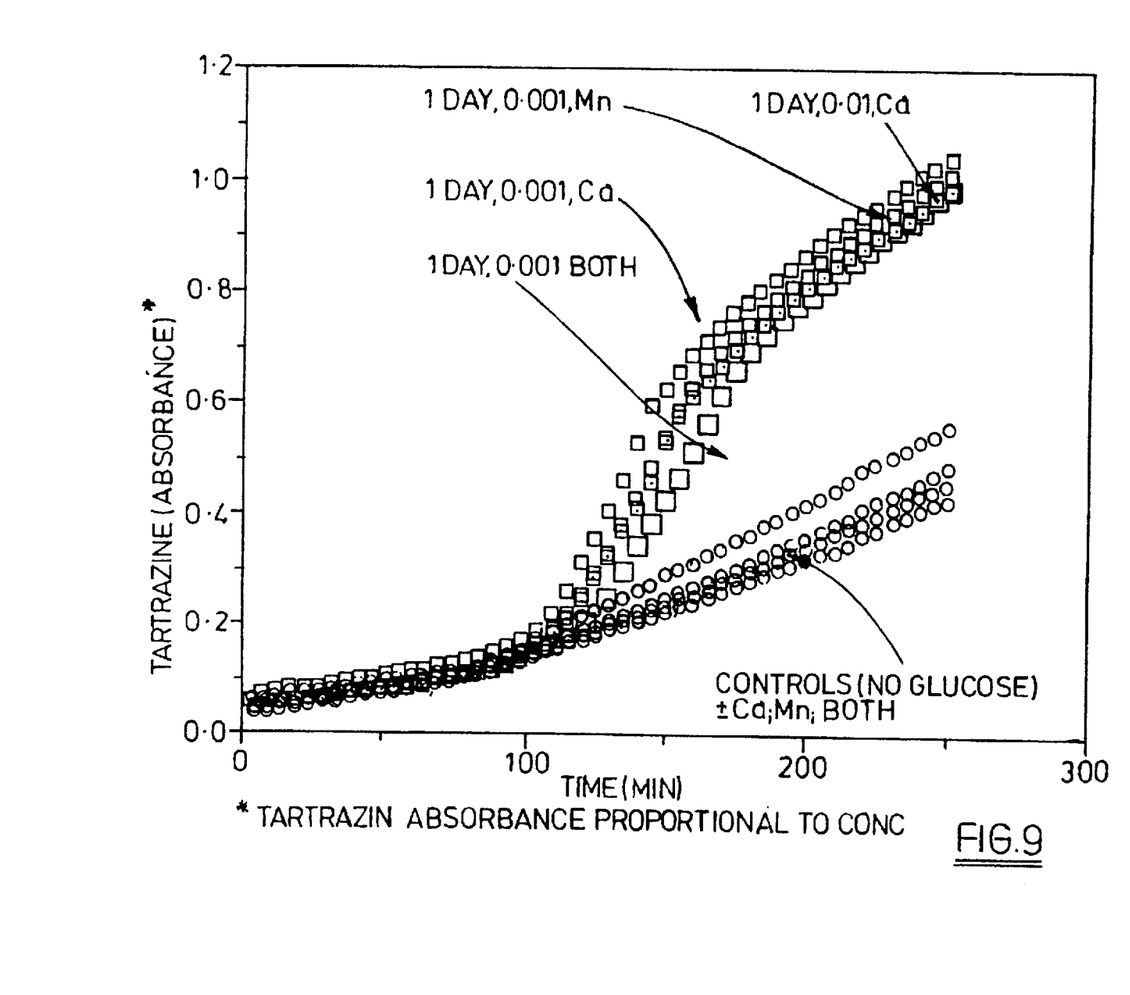

FIG. 9 shows the response of the system to $Ca^{++}$ and $Mn^{++}$ ions which are known to be required for carbohydrate binding to lectin molecules. The control preparation already contained a trace of both ions but the effect of each was monitored in case it had an effect on the response. $Ca^{++}$ and $Mn^{++}$ ions did not effect the system either alone or in combination.

Figure 10:
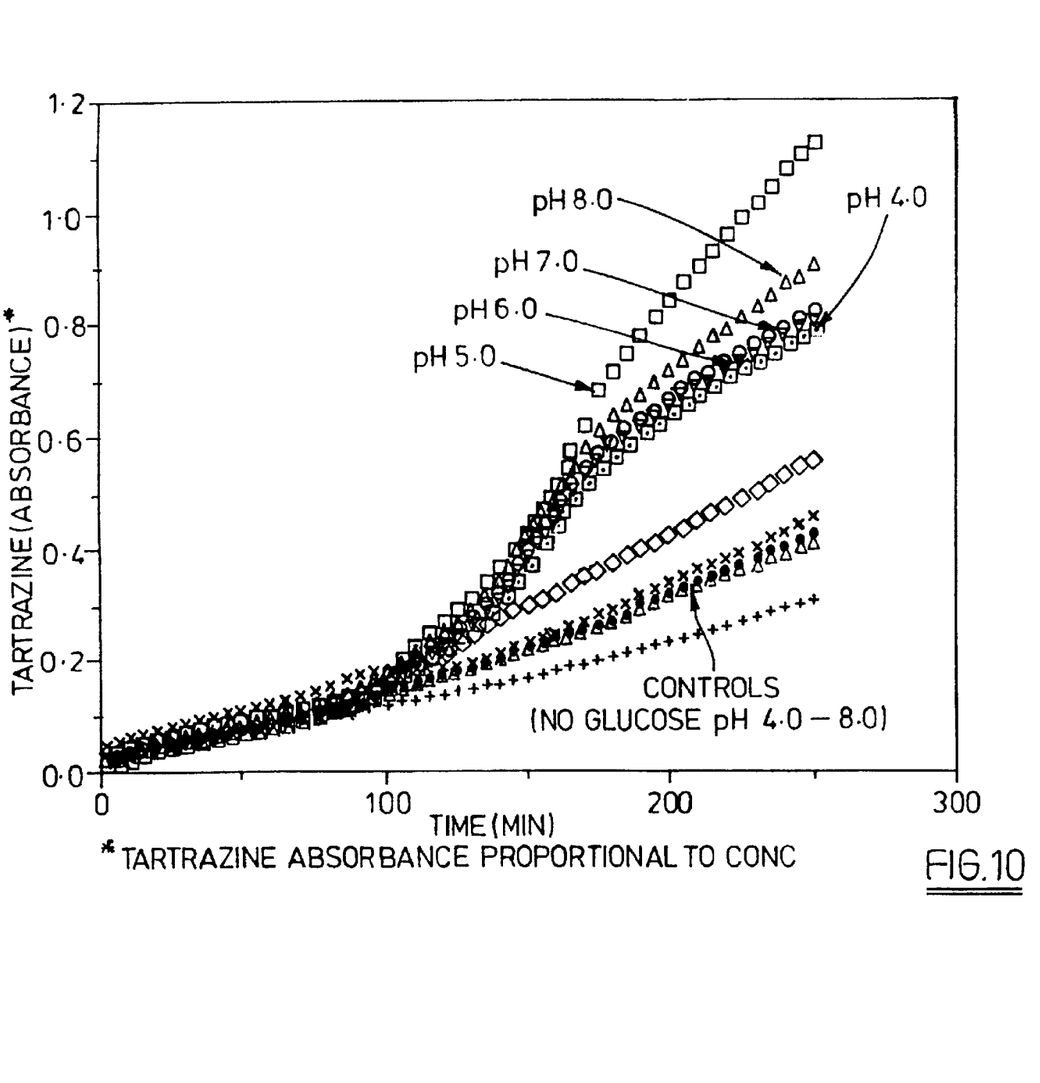

FIG. 10 shows the effect of pH on the system. pH changes from 4.0 to 8.0 had very little effect. It is assumed that the gelatinous surroundings may protect the lectin from being affected by pH as normally between pH 5.8 and 7.0 lectins exist as tetramers, while dimers and aggregates exist below and above this range respectively. Thus this system will work in the adverse pH conditions of the digestive tract.

It will be appreciated that it is not intended to limit the invention to the above example only, many variations, such as might readily occur to one skilled in the art, being possible, without departing from the scope thereof.

For example, when administering anything other than insulin or a drug which is intended to control blood sugar, the drug or agent may be released not by a feed-back mechanism but by a controlled administration of sugar, bringing literally tc life the notion of a spoonful of sugar making the medicine go down.

The receptor may be any molecule, natural or engineered, having binding sites for complex branched substrates which would form a gel on binding, but would be displaceable by the 'free' substrate which may be naturally or artificially induced to effect release of a drug or other agent. Lectins other than concanavalin-A, which may be non-toxic or less toxic, may be used, for example, the pea (*Pisium sativum*) lectin.

What is claimed is:

1. A method for producing a drug system for delivering a drug for the treatment of a condition, comprising the steps of:

providing a macromolecule having a plurality of binding sites for a physiological moiety;

providing a polymeric cross linking agent having a plurality of said physiological moieties bound at terminal positions;

anchoring the macromolecule to the polymeric cross linking agent by a covalent bond;

providing the drug; and combining the drug with the macromolecule bonded to the polymeric cross linking agent, whereby the plurality of binding sites bind to the plurality of physiological moieties to form a gel matrix having a conformation which reversibly immobilizes the drug, wherein the gel matrix undergoes a conformational change upon exposure to free said physiological moieties thereby mobilizing the drug.

2. A method according to claim 1, wherein the drug comprises a naturally occurring biological agent.

3. A method according to claim 2, wherein the biological agent is a hormone.

4. A method according to claim 3, wherein the hormone is insulin.

5. A method according to claim 1, wherein the binding macromolecule is a lectin.

6. A method according to claim 5, wherein the lectin is concanavalin A, a jack bean lectin.

7. A method according to claim 5, wherein the lectin is a pea lectin.

8. A method according to claim 1, wherein the polymeric crosslinking agent is a carbohydrate.

9. A method according to claim 8, wherein the carbohydrate is dextran, wherein terminal glucose moieties on the dextran bind to the receptor.

10. A method according to claim 1, wherein the physiological moiety is glucose.

11. A method according to claim 1, wherein the drug is immobilized in the matrix when terminal glucose molecules on dextran bind to concanavalin A to form a gel.

12. A method according to claim 1, wherein the conformational change is an ungelling of the matrix.

13. A method for producing a drug system for delivering a drug for the treatment of a condition, comprising the steps of:

providing a macromolecule having a plurality of binding sites for a physiological moiety;

providing a polymeric cross linking agent having a plurality of said physiological moieties bound at terminal positions;

anchoring the macromolecule to the polymeric cross linking agent by a covalent bond;

providing the drug; and combining the drug with the macromolecule bonded to the polymeric cross linking agent, whereby the plurality of binding sites bind to the plurality of physiological moieties to form a gel matrix having a conformation which reversibly immobilizes the drug, wherein the gel matrix undergoes a conformational change upon exposure to free said physiological moieties thereby mobilizing the drug, wherein the drug system is targeted to at least one mono- and/or di-saccharide, wherein the mono- or di-saccharides are selected from $\alpha$-D-mannose, $\alpha$-D-glucose, $\alpha$-fructose, $\beta$-fructose, or maltose or di-glucose with $\alpha$-linkage.

14. A method according to claim 13, wherein the drug comprises a naturally occurring biological agent.

15. A method according to claim 14, wherein the biological agent is a hormone.

16. A method according to claim 15, wherein the hormone is insulin.

17. A method according to claim 13, wherein the binding macromolecule is a lectin.

18. A method according to claim 17, wherein the lectin is selected from concanavalin A, a jack bean lectin or a pea lectin.

19. A method according to claim 13, wherein the polymeric crosslinking agent is a carbohydrate.

20. A method according to claim 13, wherein the physiological moiety is glucose.

* * * * *

UNITED STATES PATENT AND TRADEMARK OFFICE
CERTIFICATE OF CORRECTION

PATENT NO.     : 6,410,053 B1
DATED          : June 25, 2002
INVENTOR(S)    : Margaret Joan Taylor It is certified that error appears in the above-identified patent and that said Letters Patent is hereby corrected as shown below:

<u>Title page,</u>
Item [54], replace "REVERSIBLE CROSS-LINKED GEL" with -- DRUG SYSTEM --

<u>Column 2,</u>
Line 3, replace "without-forming" with -- without forming --.
Line 21, replace "αD-mannose" with -- α-D-mannose --.
Line 24, replace "may-not" with -- may not --.

<u>Column 3,</u>
Line 10, replace "mnolecules" with -- molecules --.
Line 25 to 26, replace "200-mg" with -- 200 mg --.
Lines 27 and 46, replace "4-10º C. for" with -- 4-10º C for --.
Line 55, replace "above 15º C. for" with -- above 15º C for --.
Line 63, replace "ie." with -- i.e., --.

<u>Column 4,</u>
Line 20, replace "repose" with -- response --.
Line 46, replace "tc" with -- to --.

Signed and Sealed this

Fifteenth Day of April, 2003

JAMES E. ROGAN
*Director of the United States Patent and Trademark Office*